United States Patent [19]

McDaniel

[11] Patent Number: Plant 7,495

[45] Date of Patent: Apr. 9, 1991

[54] PYRETHRUM PLANE NAMED ARIZONA

[75] Inventor: Robert G. McDaniel, Tucson, Ariz.

[73] Assignee: Arizona Technology Development Corporation, Tucson, Ariz.

[21] Appl. No.: 332,611

[22] Filed: Mar. 31, 1989

[51] Int. Cl.[5] ..... A01H 5/00

[52] U.S. Cl. ..... Plt./74

[58] Field of Search ..... Plt. 68, 74

[56] References Cited

U.S. PATENT DOCUMENTS

P.P. 5,848 1/1987 Bhat et al. ..... Plt. 74

*Primary Examiner*—James R. Feyrer

*Attorney, Agent, or Firm*—David G. Rosenbaum

[57] ABSTRACT

A new and distinct cultivar of *Chrysanthemum cinerariaefolium* known by the cultivar name Arizona, and particularly characterized by the combined characteristics of high pyrethrin content, environmental stress tolerance, uniform flower stalk extension and substantially erect growth.

4 Drawing Sheets

BACKGROUND OF THE INVENTION

The present invention comprises a new and distinct variety of *Chrysanthemum cinerariaefolium*, which has been designated by the cultivar name Arizona. *Chrysanthemum cinerariaefolium*, Vis. Arizona is the product of selective breeding program having the objective of creating new Chrysanthemum cultivars whose characteristics include environmental stress tolerance, high pyrethrin content, uniform flower stalk extension and substantially erect growth. The new Chrysanthemum plant is largely sterile. *Chrysanthemum cinerariaefolium* Vis. Arizona is the result of a recurrent selection breeding program started in 1979 from *Chrysanthemum cinerariaefolium* seed of unknown origin. The breeder stock is held by the University of Arizona, College of Agriculture, Department of Plant Sciences, Tuscon, Ariz.

BREEDING METHODOLOGY

*Chrysanthemum cinerariaefolium* seed of unknown origin was germinated and grown in a greenhouse. In 1980, vigorous transplants were chosen from the greenhouse grown nursery stock and transplanted to a field at the University of Arizona, Marana Agricultural Center. Over 99% of the transplants failed to survive the either the high summer temperatures (daytime temperatures) ranges from about 95° F. to about 115° F.), exhibiting crown rots associated with high night temperatures (ranging from about 80° F. to about 100° F.), the subfreezing winter nights and the need to exhibit a measure of drought tolerance between scheduled irrigations. Some of the survivors set seed which was outcrossed as *Chrysanthemum cinerariaefolium* was self-incompatible.

The seed from the surviving plants was harvested, germinated in a growth chamber, and transplanted to the greenhouse. The young plants were transplanted to an adjacent field area to establish a second field test and grown in 24" row spacings on cotton beds with 40" centers. After over one year in the field, the best of the second generation plants were split into several pieces. These asexual propagules were planted in rows and used to evaluate the phenotypes of the plants. Phenotypes which exhibited a planar flowering habit by flowering at the top of the plant, lodging resistance and ease of picking were selected. All breeding lines were evaluated for pyrethrin content and quality, determined by the relative proportion of the six distinct chemical components of pyrethrin.

Likely, due to the extreme climatic stresses at the Marana field, some of the clones showed a biannual tendency. Because of this and other field conditions at that location which made continued growth undesirable, the most promising asexual propagules, their seed and some seedling plants were then transplanted over a period of time to the University of Arizona Campus Agricultural Center in 1983 in three adjacent field areas A, B and C. In 1984 and 1985 the best of these materials, sister lines grown from seed and asexual propagules from the greenhouse were transplanted to a new field area D. Phenotypes and pyrethrin content and quality were evaluated annually.

To test the stress tolerance of the plants to high temperatures and salinated soil, in 1981 seedlings from the greenhouse were transplanted a field plot was established at the University of Arizona, Safford Agricultural Center. These clones were irrigated with salinated water which resulted in soil salinity levels approaching ⅓ that of sea water. Survival rates of these transplants were extremely low and the plants were badly stunted. Pyrethrin levels were lower than desired.

All surviving clones from the Safford field were transplanted back to the University of Arizona Campus Agricultural Center in 1985 in a new field area E, and seed from the most promising "salt tolerant" clones were replicated in 30 foot half sib progeny tests.

At the same time 30 rows were planted in a new field area F at the University of Arizona Campus Agricultural Center. Each of these thirty rows were divided into seven, thirty foot sections. Seed from the most promising clones growing in field areas A through D were sown head-to-row in randomized duplicate replications within field area F. Field area F was divided into three subplots with randomizations within each sub-plot. Rows 1 through 6 were half sib progeny of clones which displayed excellent lodging resistance, but on which pyrethrin content data were imcomplete at planting time. Rows 7 through 21 comprised half sib progeny whose parent clones exhibited good lodging resistance, planar flowering habit and a relatively high pyrethrin content compared to the base population. Rows 22 through 29 were half sib progeny of other promising clones, and seed from all other promising clones as well as four entries comprising a composite "bulk" of seed from all field F entries. After one season, the three top pyrethrin producing plants from field area D were split and established in 30 foot areas of field area F to enable evaluation of pyrethrin levels from genetically identical clones.

The breeding program has produced three distinct germplasms, one of which was asexually propagated and is referred to as Clone CA 87 F 4-101. This clone was originally identified in a high pyrethrin producing clonal progeny in the field at the University of Arizona, Marana Agricultural Center. The progenitors of Clone CA 87 F 4-101 were maintained by recurrent selection for high pyrethrin content, planar flowering habit, lodging resistance and ease of picking in the original test area at the University of Arizona, Campus Agricultural Center. This clone is the asexual propagule of a single plant (identified as CA 85 D 7-54) which was in turn selected from the half sib progeny of a plant identified as CA 83 A 7-13. Seven daughter clones (identified as CA 87 F 4-101; 102; 103; 104; 105; 106 and 107) of the single parent plant have been evaluated for agronomic phenotype consistency and pyrethrin content and quality.

PYRETHRIN ANALYSIS METHODOLOGY

Flowers are harvested in April at the ½ to ¾ disc floret open developmental stage. Flower samples are randomly collected and harvested onto ice and stored in darkness until transported from the field to the laboratory. Flower samples are then counted, weighed and stored at −70° C. The flowers are freeze dried in a lyophilizer for at least 24 hours, after which dry weights are taken. Flowers are then ground for 20 to 25 seconds in a grinder yielding a somewhat coarse yellow powder. Ground samples then are stored at −70° C. until extracted.

For pyrethrin extraction, 0.2 g of the ground flowers are added to a 50 ml culture tube, 10 ml of spectograde hexane is added to the ground flowers and the tubes agitated slowly on a rotator for at least ten minutes. The tube is then emptied into a miracloth square and decanted into a second 50 ml tube. The ground flower cake is returned to the original tube, another 5 ml of hexane is added and the sample is again mixed on the rotator. The contents are again decanted into a miracloth square and the flower cake squeezed manually to expel all solvent into the second tube combining it with the first washing. The final volume of hexane flower extract is adjusted to 12 ml by evaporation under nitrogen, or by adding additional hexane. 3 ml of extract is pipetted into a serum collected vaccutainer tube and evaporated to dryness under nitrogen. The sample is stored under refrigeration until needed.

The evaporated sample residue is redissolved in 3 ml of HPLC grade methanol by vortexing for 30 seconds. The dissolved sample is filtered through a Gelman 0.45μ Acrodisc syringe into a 5 ml culture tube and stored in a light-proof box under refrigeration until assayed.

Quantitative analysis of the pyrethrin content of the samples are carried out using a Varex Rosa-1 autosampler and injector interfaced with a Beckman dual pump 421A controlled, model 165 variable wavelength detector high performance liquid chromatograph, linked with a Beckman 427 microprocessor-controlled integrator. An Upchurch Scientific pre-column filled with Altech C-18 pre-column packing was mounted ahead of a Beckman Ultrasphere C-8 (or C-18) analytical column. The wavelength utilized was 229 nm, which was determined to be optimum to resolve the major pyrethrin components, based upon analysis of extinction coefficients of each of the six pyrethrin components across an array of wavelengths. The range of the instrument was set at 0.2AUFS.

At the time of sample injection, the dual pump system was programmed to deliver a 50/50 HPLC grade acetonitrile/double distilled, degassed water proportion. Two minutes after injection of the sample through a 10 μl loop, the gradient was programmed to increase at the rate of 1 and ⅔% acetonitrile per minute, for six minutes. The rate of change is then decreased to 0.93% acetonitrile per minute for 25 minutes. All pyrethrin peaks elute within 30 minutes. At the end of a 33 minute run, the acetonitrile is at 73.25%. A clean out step of 50/50 acetonitrile is programmed for 10 minutes between each sample injection. Time between automatic sample injections is 46 minutes.

All six pyrethrin components, i.e. Pyrethrin I, Pyrethrin II, Cinerin I, Cinerin II, Jasmolin I and Jasmolin II, are resolved as separate peaks, electronically integrated and expressed as area units at a given retention time (RT). Such integrations are highly repeatable over the several week period necessary for analysis of a years flower sample data. One or more standard pyrethrin samples is injected every few samples, and the integrated area of the individual pyrethrin components of this industry analyzed sample (Johnson Wax, East African Kenyan Board analyzed standard mixture 304) are used to quantify pyrethrins in Arizona grown clones.

Flowers of the daughter clones exhibit superior pyrethrin content when compared with the majority of other clones tested. High performance liquid chromatography analyses of hexane extracted, freeze dried flowers are presented in Table 1. The pyrethrin content of the clones, as measured by levels of Pyrethrin I (Chrysanthemum-monocarboxylic acid having the formula $C_{21}H_{28}O_3$ or the ester thereof), Pyrethrin II (Chrysanthemum-dicarboxylic acid having the formula $C_{22}H_{28}O_5$ or the ester thereof), Cinerin I, Cinerin II, Jasmolin I, Jasmolin II and the Pyrethrin I/Pyrethrin II ratios, which meet or exceed that of the Authentic Kenyan pyrethrin standard. Table 2 presents agronomic characteristics of CA 85 D7-54 daughter clones which indicate markedly consistent plant height, flower diameter and flower weight between the daughter clones.

TABLE 1

| | Peak areas at 229 nm × 10[1] | | | | | |
|---|---|---|---|---|---|---|
| Compared | RT[1] | Authentic Kenyan STD 304 | RT | Clone CA 87 F 4-103 | RT | Clone CA 87 F 4-106 |
| Cinerin II | 18.9 | 70.9 | 18.7 | 39.8 | 18.7 | 37.5 |
| Pyrethrin II | 19.6 | 468.7 | 19.4 | 357.9 | 19.4 | 438.1 |
| Jasmolin II | 22.7 | 39.5 | 22.5 | 21.4 | 22.4 | 28 |
| Cinerin I | 28.8 | 73.9 | 28.5 | 47.6 | 28.4 | 46 |
| Pyrethrin I | 29.3 | 693.7 | 29 | 621.4 | 28.9 | 751.2 |
| Jasmolin I | 33 | 29 | 32.8 | 29 | 30.0 | 37 |
| Py I/Py II Ratio[2] | | 1.48 | | 1.74 | | 1.71 |

[1]RT = Retention Time (Min.)
[2]Not corrected for molar extinction coefficient differences

TABLE 2

| Clone I.D.[1] | Fresh wt./g/100 flowers | Dry wt./g/100 flowers | Flower Head diameter mm | Plant height[2] cm |
|---|---|---|---|---|
| CA 88 F 4-103 | 96 | 20 | 14.2 | 81 |
| CA 88 F 4-104 | 82 | 19 | 14.2 | 85 |
| CA 88 F 4-106 | 121 | 26 | 15.7 | 81 |
| CA 88 F 4-107 | 85 | 27 | 15.2 | 84 |

[1]Clones are daughter clones of CA 85 D7-54 and were harvested on different dates accounting for some morphological variance.
[2]Clones differed in overall crown size, also accounting for some morphological variance.

TABLE 3

| Year | Genotype | Py I/Py II Ratio | Percent Pyrethrins |
|---|---|---|---|
| 1986 | Kenyan Std. 304 | 1.42 | 2.00 |
| | D 7-54 | 1.18 | 2.09 |
| | D 7-19 | 1.33 | 1.83 |
| 1987 | Kenyan Std. 304 | 1.42 | 2.00 |
| | F 4-101 | 1.90 | 2.03 |
| | F 4-117[1] | n/a | n/a |
| 1988 | Kenyan Std. 304 | 1.36 | 2.00 |
| | F 4-101 | 1.56 | 1.95 |
| | F 4-117 | 1.61 | 2.25 |

[1]Flowers from Clone F-117 were not picked in 1987 due to small crown size.

It has been found that the balance of pyrethrin isomers is under very strict genetic control and serves as a unique molecular fingerprint of each individual pyrethrin clone. This characteristic is readily discernable is asexually propagated plant material. Clone CA 87 F 4-101 was found to be sterile and did not set viable seed even when pollinators were present. Thus, propagation is possible only through asexual means, and the daughter clones of CA87 F 4-101 were all identical.

The accompanying photographic drawings show typical inflorescence and foilage characteristics of CA 87 F 4-101 with the colors being as true as possible with such type of illustrations.

Figure 1:
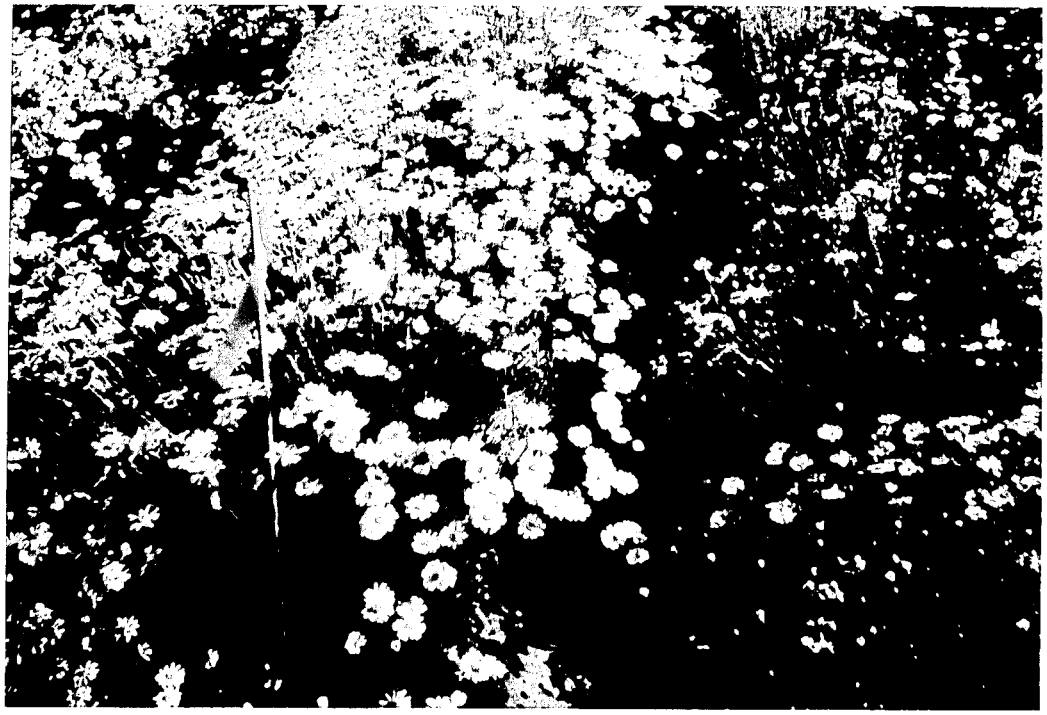
FIG. 1 shows a row of the selected clone "Arizona" (CA 87 F 4-101) marked with a red flag, alongside rows of half sibs; and illustrates rows of half sibs; and illustrates the earlier, more profuse and uniform blooming, erect flower stems and uniform height as compared to half sib clones depicted.
Figure 2:
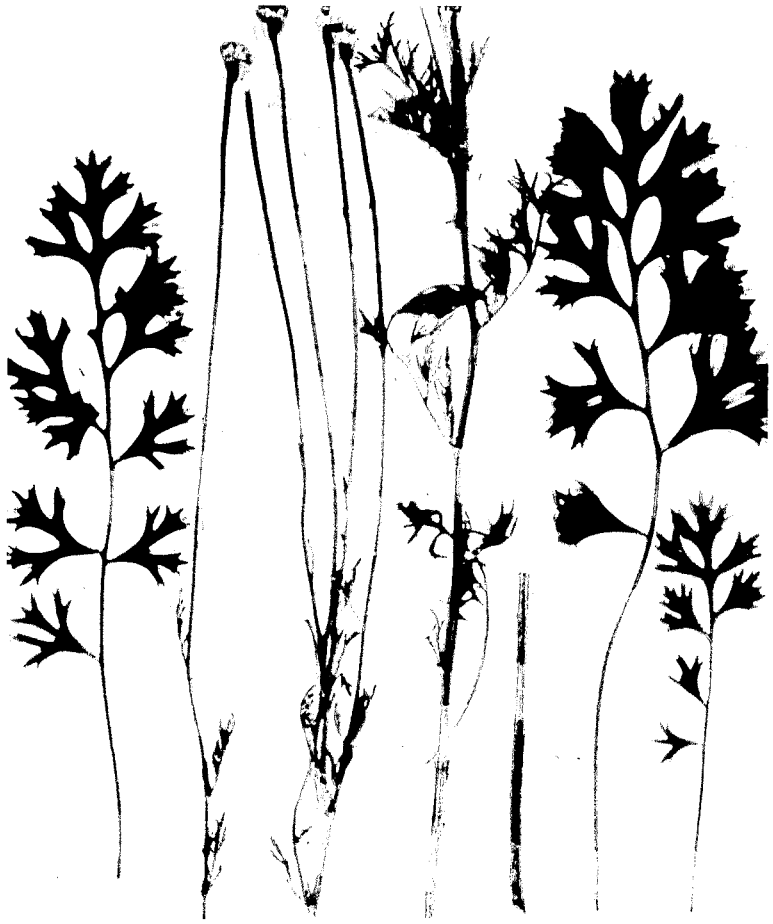
FIG. 2 illustrates a pressed herbarium specimen designated *Chrysanthemum cinerariaefolium* Vis Arizona, showing a single mature flowering stem and typical leaves of the claimed variety sectioned for convenience in pressing.
Figure 3:
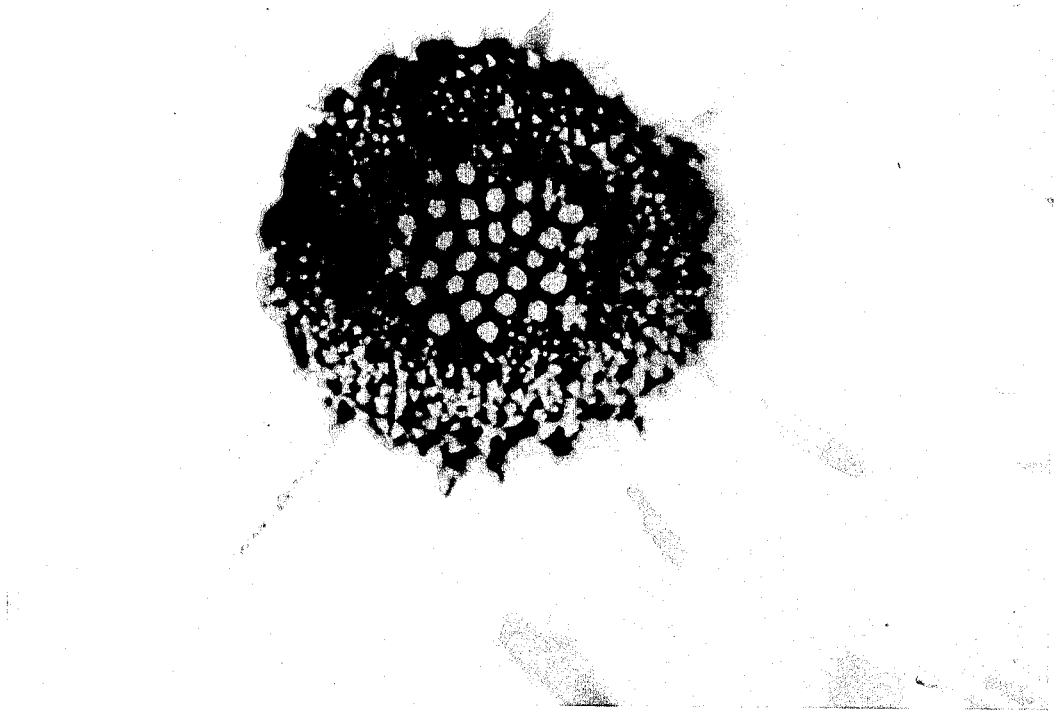

FIG. 3 illustrates a close-up of a single normal outcrossing fertile clone, which shows a halo of open florets noticeably raised above the surface of both the disc and ray florets such as that disclosed in U.S. Plant Pat. No. 5,848 issued Jan 6, 1987 to Bhat et al. entitled "Chrysanthemum Plant named Hypy".

Figure 4:
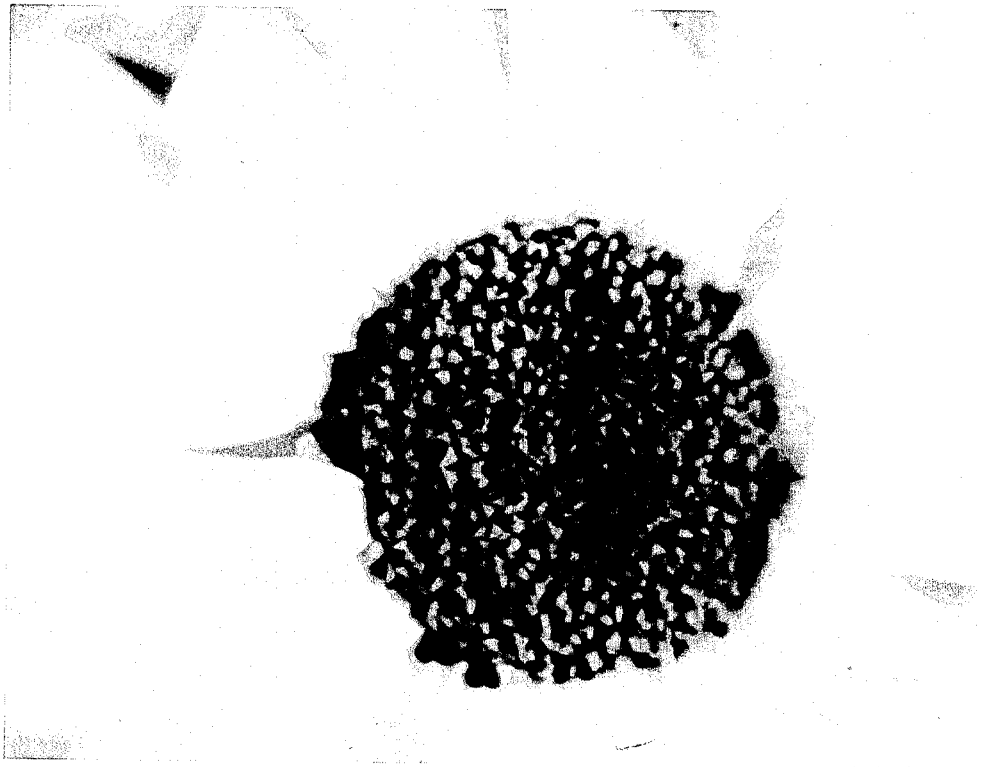

FIG. 4 illustrates a typical flower of CA 87 F 4-101 at the same developmental stage as that illustrated in FIG. 3, emphasizing the fully developed wide-open florets characteristic of this sterile clone.

Figure 5:
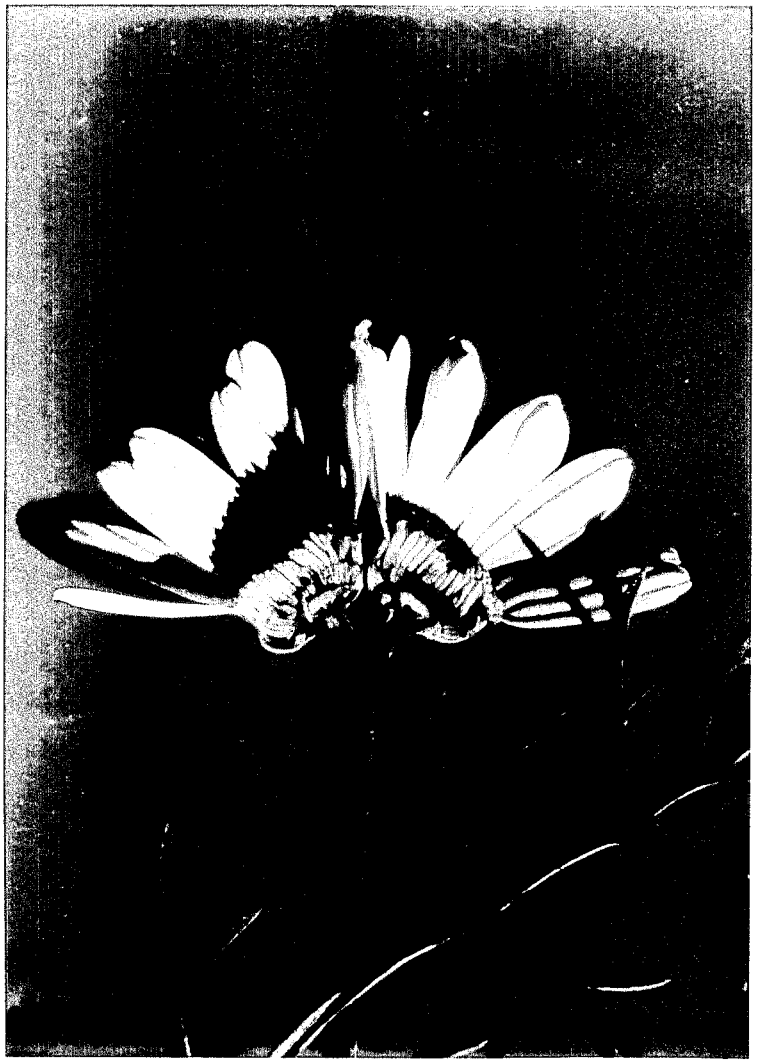

FIG. 5 illustrates a vertical section through the middle of the flower showing the shape of the receptacle and lengths of the ovary, tubular disk floret and pedals of the ray florets.

Figure 6:
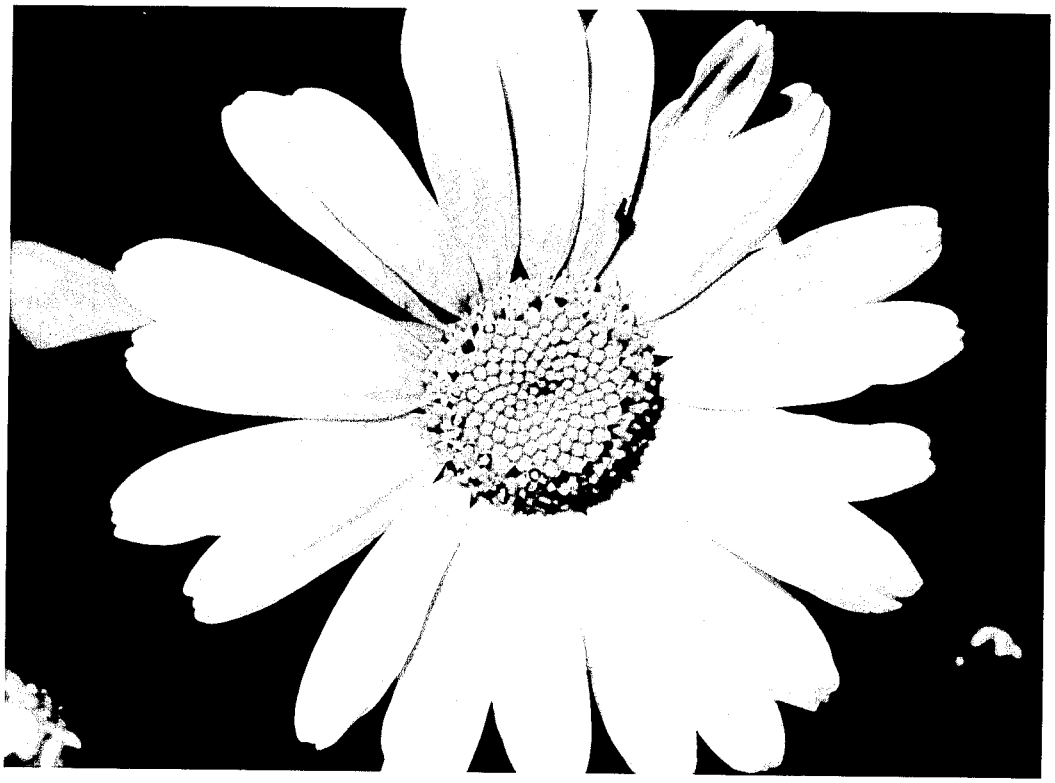

FIG. 6 illustrates a typical flower of *Chrysanthemum cinerariaefolium* Vis Arizona showing the florets and petals characteristic of this clone.

Clone CA 87 F 4-101 has very large flowers, prolific flowering and excellent vigor which correlate with good lodging resistance. In comparison with a normal, outcrossing fertile clone, which shows a halo of open florets noticeably raised above the surface of both the disc and ray florets, a typical flower of CA 87 F 4-101 at the same developmental stage exhibits a lack of developed open florets. (FIGS. 3 and 4). This clone blooms synchronously, and averaged 300–400 flowers per clone. However, mature clones of fertile, sister lines have averaged approximately 800 flowers per plant. Pyrethrin analysis of this clone, a sterile sister clone (designated F 4-117) and Kenyan Standard 304, show pyrethrin content of about 2% or greater as set forth in Table 3.

Typical flowers of the clone contain considerably less pollen than the usual flower. Anthers contain what appear to be grayish, incompletely matured pollen grains. Some pollen looks fully developed and can sometimes be observed in a few anthers, depending upon the environment. Florets of the clone open more rapidly towards the center than the usual flowers. FIGS. 3 and 4 show flowers at the same relative stage of development; the flower of the clone has completely opened florets, whereas the flower of the other lines have only partially opened florets at the same stage of development. The clone is characterized by widely open florets, which are typical of sterile or partly sterile flowers from many species. The ray florets of the clone are believed to be completely sterile and the florets of the clone rapidly open from outside toward center. Two separate field plantings of seed from the clone have failed to germinate, whereas adjacent plantings of seed from other plants succeeded.

Flowers of the clone have a strong scent which has been described by observers as an intense musty, aromatic chemical smell. Splitting the flower in half greatly intensifies the scent, so it does not appear to be a nectar volatile aroma. Flowers typically display from 22 to 27 pedals, compared to 19 to 22 of the typical pyrethrum flower. The clone has thicker stems which provide visually greater lodging resistance than other plants of similar height. Flowering stems of every other plant which are 90% as tall or taller than the clone fall over under field conditions. Peak bloom dates were Apr. 25, 1989, Apr. 29, 1988 and Apr. 28, 1987. Plants heights averaged over 90 cm; flowers per plant averaged over 400 (with a maximum of 500+); typical plants ranged from 50 to 80 cm with an average of about 65 cm; flowers per plant ranged from 4 to approximately 450. A typical plant flower head diameter ranged from 9 mm to 14.3 mm with a mean of about 12.8 mm. Flowers per stem of the clone averaged 5 (range of 1–10 with considerable variability); while the conventional plant averages 3 to 4 flowers on virtually every stem. The clone splits readily, and the splits exhibit high field survival rates (over 90%) and a medium sized plant will usually yield 15 to 45 small to medium size splits, each with a sturdy, untwisted root system. All clones derived from the original plant bloomed in close synchrony, within 2 to 3 days, and reached peak flower opening rapidly, retained pyrethrum content for at least two weeks and have agronomically favorable attributes of flowers born at the same height, enabling the flowers to be mechanically harvested "once over".

The physical size of the clone relative to the great majority of other plants with similar genetic background, including sterility, plant height, flower diameter, pedal member, stem diameter and number of flowers per stem indicates this plant may be a triploid.

It has been found that the clone exhibits optimum growth patterns in a wide range of elevations and stressful growing environments. Table 4 summarizes environmental responses of *Chrysanthemum cinerariaefolium* Vis. Arizona across a range of Arizona environments:

TABLE 4

| Location | Elevation (m) | Climatology and Agronomics |
|---|---|---|
| Lakeside | 2137 | Snow cover protects crowns, cold/dry winter kill plants. |
| Elfrida | 1213 | Excellent survival; plants die back to crown in winter. |
| Safford | 900 | Plants under salt stress, perennial habit, small stature, lower pyrethrin levels. |
| Tucson | 714 | Near optimum location, high pyrethrin levels, good survival at temperatures in range of about 17° F. to about 111° F. |
| Tucson | 699 | Good environment, high soil nitrates burnt many transplanted splits. |
| Marana | 598 | More extreme temperatures in the range of about 15° F. to about 115° F. and high summer nighttime temperatures over 80° F. elicit crown rots. |
| Yuma | 50 | High summer temperatures and humidity cause fungus crown diseases and kill plants. |

In describing the colors, reference has been made to the book *R.H.S. Colour Chart,* published by The Royal Horticultural Society, London, England in association with the Flower Counsil of Holland.

INFLORESCENCE

A. Capitulum: Flat, daisy, diameter across face approximately 40–80 mm.

B. Corolla of ray florets: White, bright tonality.

C. Corolla of disk florets: Approximately orange-yellow 17A; (fresh colors); approximately yellow 7A to 13A (dried colors).

D. Reproductive organs: Male flowers reduced in number and greatly reduced in function. Female flowers, present in disk florets, uncertain presence in ray florets.

PLANT

A. Foliage:

*Upper leaves.*—Approximately green 137C to 137D.

*Midplant leaves.*—Green 137B to 137C.

*Lower leaves.*—Green 137A, 137B to 137C.

*Underside of leaves.*—Approximately green 147B to 147C.

It can be appreciated by those skilled in the art that a new asexually reproduced pyretrum plant, designated *Chrysanthemum cinerariaefolium* Vis. Arizona has been developed which exhibits the following characteristics:

1. Stress tolerance to high heat and mild freezes.
2. Adaptation to Arizona latitude and elevation.
3. Pyrethrin content of 2% or more.
4. Balance of Pyrethrin content I to Pyrethrin II (PyI/PyII ratio) close to that of preferred East African pyrethrins.
5. Sterility.
6. Readily asexually propagated from splits.
7. Excellent plant vigor and spring regrowth.
8. Synchronous flowering. All flowers mature at nearly the same time, all daughter clones bloom together.
9. Vigorous and profuse flowering.
10. Planar flowering habit.
11. Large flowers exhibiting goof flower form.
12. Plant color of medium green with a slight grey undertone.
13. Medium to large cut leaves.
14. Tall and erect phenotype.
15. 100 flower dry weight is about 23.0 grams.
16. Flowers are easily broken off stems, flowers normally retain no stem when picked.
17. Perennial habit.
18. Good lodging resistance, due to large, stiff stems.

Thus, a new and distinct cultivar of *Chrysanthemum cinerariaefolium* designated Arizona has been described which exhibits both high pyrethrin content and environmental stress tolerance. The cultivar Arizona may be asexually reproduced to yield propagules of like phenotypes, the uniform phenotype having the same genetic fingerprint of the six pyrethrin isomers as that of the parent clone, thereby facilitating identification of the plant lineage.

I claim:

1. A new and distinct cultiar of *Chrysanthemum cinerariaefolium* plant known by the cultivar name Arizona, and particularly characterized as to uniqueness as described and illustrated herein by the combined characteristics of high pyrethrin content, environmental stress tolerance, uniform flower stalk extension and substantially erect growth.

* * * * *

Chrysanthemum cinerariefolium Vis 'Arizona'

UNITED STATES PATENT AND TRADEMARK OFFICE

CERTIFICATE OF CORRECTION

PATENT NO. : Plant 7,495

DATED : April 9, 1991

INVENTOR(S) : Robert G. McDaniel

It is certified that error appears in the above—identified patent and that said Letters Patent is hereby corrected as shown below:

ON THE TITLE PAGE: Item [54]

In the title, delete "PLANE", insert therefor "PLANT"

Column 1, line 27, delete ")" after "temperatures"

Column 5, line 49, delete "pedals", insert therefor --petals--

Column 6, line 38, delete "pedals", insert therefor --petals, as illustrated in Fig. 6,--

Column 6, line 45, delete "90", insert therefor "80"

Column 6, line 49, after "diameter", insert --, not including petals,--

Column 8, line 43, (line 1 of Claim 1), delete "cultiar", insert therefor --cultivar--

Signed and Sealed this

Fifteenth Day of December, 1992

*Attest:*

DOUGLAS B. COMER

*Attesting Officer*

*Acting Commissioner of Patents and Trademarks*